(12) United States Patent
Saito et al.

(10) Patent No.: US 12,357,771 B2
(45) Date of Patent: Jul. 15, 2025

(54) BLOOD VESSEL SPECIFYING DEVICE AND BLOOD VESSEL SPECIFYING METHOD

(71) Applicants: Kabushiki Kaisha Nihon Micronics, Tokyo (JP); Hirosaki University, Aomori (JP)

(72) Inventors: Yuki Saito, Saitama (JP); Yoshiyuki Fukami, Ibaraki (JP); Hiroshi Kamiya, Kanagawa (JP); Osamu Arai, Tochigi (JP); Kazuhiko Sasagawa, Aomori (JP); Koichi Sagawa, Aomori (JP); Yasutaka Hanada, Aomori (JP); Toshiro Ono, Kanagawa (JP)

(73) Assignee: Kabushiki Kaisha Nihon Micronics, Musashino (JP)

( * ) Notice: Subject to any disclaimer, the term of this patent is extended or adjusted under 35 U.S.C. 154(b) by 740 days.

(21) Appl. No.: 17/611,078

(22) PCT Filed: Feb. 28, 2020

(86) PCT No.: PCT/JP2020/008320
§ 371 (c)(1),
(2) Date: Nov. 12, 2021

(87) PCT Pub. No.: WO2020/230408
PCT Pub. Date: Nov. 19, 2020

(65) Prior Publication Data
US 2022/0257874 A1    Aug. 18, 2022

(30) Foreign Application Priority Data

May 15, 2019 (JP) .................. 2019-091843

(51) Int. Cl.
*A61M 5/42* (2006.01)
*G06T 7/00* (2017.01)

(52) U.S. Cl.
CPC .......... *A61M 5/427* (2013.01); *G06T 7/0012* (2013.01); *A61M 2205/3313* (2013.01); *A61M 2205/502* (2013.01); *G06T 2207/30101* (2013.01)

(58) Field of Classification Search
CPC .......... A61M 5/427; A61M 2205/3313; A61M 2205/502; G06T 7/0012; G06T 2207/30101
(Continued)

(56) References Cited

U.S. PATENT DOCUMENTS 6,556,858 B1    4/2003  Zeman
2015/0065916 A1*  3/2015  Maguire .......... A61B 5/150748
                                                    600/573
(Continued)

FOREIGN PATENT DOCUMENTS

JP    2006102110 A    4/2006
JP    4555534 B2     10/2010
(Continued)

OTHER PUBLICATIONS

Yi Yan Xu Ting, Clinical Study On Standardized Seven-Step Puncture of Indwelling Needle in Pediatric Patients, Journal of Taishan Medical College, vol. 40, No. 4, Apr. 11, 2019.

*Primary Examiner* — Michael R Neff
(74) *Attorney, Agent, or Firm* — Lorenz & Kopf, LLP

(57) ABSTRACT

A blood vessel specifying device (1) includes an image processing device (31) configured to subject an image for analysis of a target part (2) to image processing to acquire blood vessel information including positions and shapes of blood vessels included in the target part (2), an evaluation device (32) configured to use the blood vessel information to assign a point rating regarding a parameter that indicates a conformity to a particular purpose with respect to the blood vessels included in the image for analysis depending on a (Continued)

degree of the conformity, and a specification device (33) configured to specify conforming blood vessels conforming to the purpose from the blood vessels included in the target part (2) in accordance with rating points of the parameter.

10 Claims, 6 Drawing Sheets

(58) Field of Classification Search
USPC .......................................................... 382/128
See application file for complete search history.

(56) References Cited

U.S. PATENT DOCUMENTS

| 2015/0356369 A1 | 12/2015 | Kitamura et al. |
| 2016/0354030 A1 | 12/2016 | Tang et al. |

FOREIGN PATENT DOCUMENTS

| JP | 2014161672 A | 9/2014 |
| JP | 6127207 B2 | 5/2017 |
| JP | 2017164046 A | 9/2017 |

\* cited by examiner

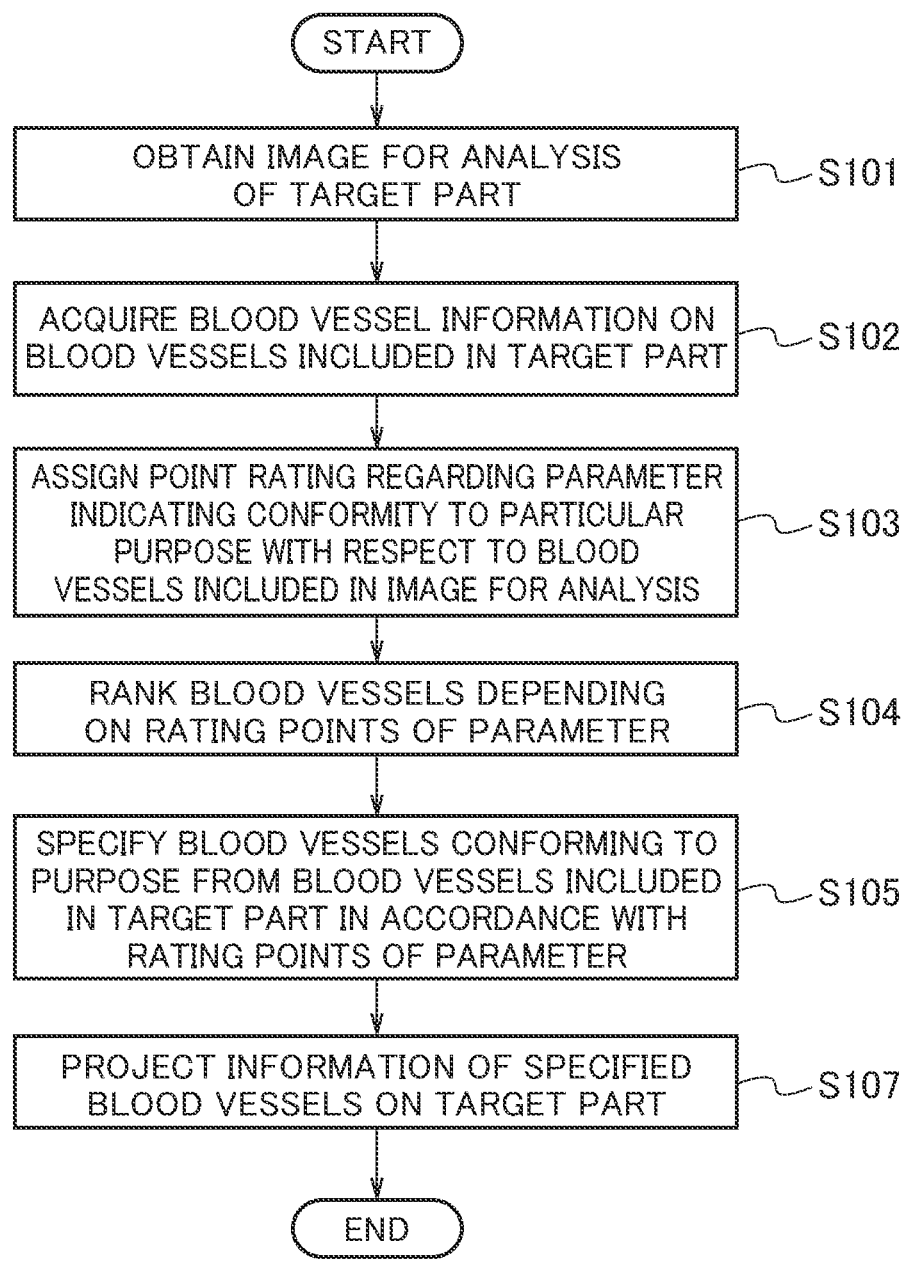

BLOOD VESSEL SPECIFYING DEVICE AND BLOOD VESSEL SPECIFYING METHOD

TECHNICAL FIELD

The present invention relates to a blood vessel specifying device and a blood vessel specifying method for specifying blood vessels.

BACKGROUND ART

A system is disclosed that displays positions of blood vessels obtained from an image indicating a part of a human body (refer to Patent Literature 1 and Patent Literature 2). A method is known, for example, that captures a part irradiated with a near infrared light by an infrared camera so as to visualize the blood vessels while taking advantage of the properties of hemoglobin that absorbs the near infrared light.

CITATION LIST

Patent Literature

Patent Literature 1: Japanese Patent No. 4555534
Patent Literature 2: Japanese Patent No. 6127207

SUMMARY OF THE INVENTION

Technical Problem

No conventional systems disclose a method that not only visualizes blood vessels but also specifies blood vessels conforming to a particular purpose. A method of displaying the positions of the blood vessels suitable for needle puncture for collecting blood, for example, still needs to be developed.

In response to this issue, the present invention provides a blood vessel specifying device and a blood vessel specifying method capable of specifying blood vessels conforming to a particular purpose.

Solution to Problem

An aspect of the present invention provides a blood vessel specifying device including an image processing device configured to subject an image for analysis of a target part to image processing to acquire blood vessel information including positions and shapes of blood vessels included in the target part, an evaluation device configured to use the blood vessel information to assign a point rating regarding a parameter that indicates a conformity to a particular purpose with respect to the blood vessels included in the image for analysis depending on a degree of the conformity, and a specification device configured to specify conforming blood vessels conforming to the purpose from the blood vessels included in the target part in accordance with rating points of the parameter.

Another aspect of the present invention provides a blood vessel specifying method includes subjecting an image for analysis of a target part to image processing to acquire blood vessel information including positions and shapes of blood vessels included in the target part, using the blood vessel information to assign a point rating regarding a parameter that indicates a conformity to a particular purpose with respect to the blood vessels included in the image for analysis depending on a degree of the conformity, and specifying conforming blood vessels conforming to the purpose from the blood vessels included in the target part in accordance with rating points of the parameter.

Advantageous Effects of the Invention

The present invention can provide the blood vessel specifying device and the blood vessel specifying method capable of specifying the blood vessels conforming to a particular purpose.

BRIEF DESCRIPTION OF DRAWINGS

FIG. 10 is a flowchart for explaining a blood vessel specifying method according to the second embodiment of the present invention.

DESCRIPTION OF EMBODIMENTS

Figure 1:
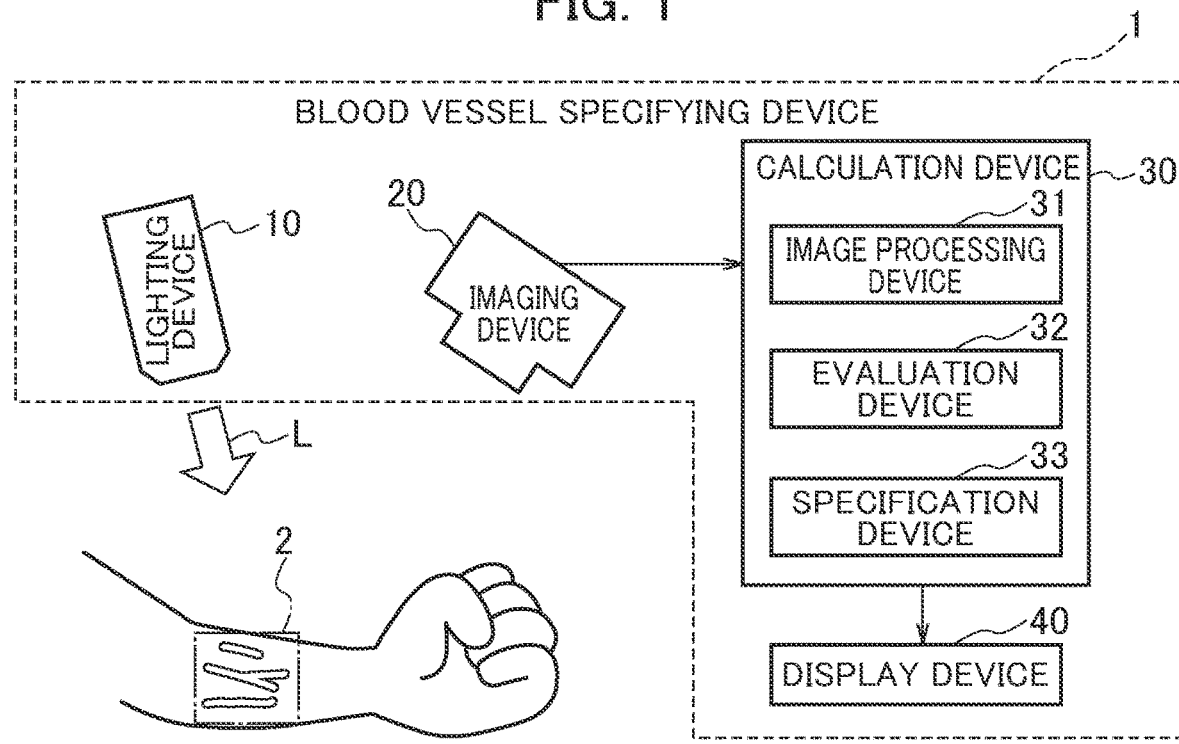
FIG. 1 is a schematic view illustrating a configuration of a blood vessel specifying device according to a first embodiment of the present invention.

Some embodiments of the present invention are described below with reference to the drawings. The same or similar elements illustrated in the drawings are denoted below by the same or similar reference numerals. It should be understood that the drawings are shown as schematic illustrations. It should also be understood that the embodiments described below illustrate devices and methods for embodying the technical idea of the present invention, but are not intended to be limited to the structures or arrangements of the constituent elements as described herein. Various modifications can be made to the respective embodiments according to the present invention in terms of the appended claims.

First Embodiment

A blood vessel specifying device according to a first embodiment of the present invention specifies blood vessels conforming to a particular purpose chosen from blood vessels included in a target part to be sampled. The following explanations are made with regard to a case in which a part of a forearm of a human body is a target part 2, as illustrated in FIG. 1. The blood vessel specifying device 1 illustrated in FIG. 1 includes a lighting device 10, an imaging device 20, a calculation device 30, and a display device 40. The calculation device 30 includes an image processing device 31, an evaluation device 32, and a specification device 33.

The lighting device 10 irradiates the target part 2 with an irradiation light L having a specific wavelength. The imaging device 20 captures the target part 2 including a region around blood vessels to obtain an image for analysis of the target part 2. The calculation device 30 specifies blood vessels, as "conforming blood vessels", that conform to a particular purpose from blood vessels included in the target part 2 based on the image for analysis. The information on the specified blood vessels is displayed on the display device 40. The blood vessel specifying device 1 is described in more detail below.

The wavelength of the irradiation light L emitted from the lighting device 10 is determined such that the imaging device 20 can capture the image for analysis in which boundaries between the blood vessels and the other regions are more distinct in the target part 2 irradiated with the irradiation light L than in the other part not irradiated with the irradiation light L. For example, a near infrared light having a wavelength in a range of about 800 nm to 900 nm may be used as the irradiation light L so as to take advantage of the properties of hemoglobin that absorbs the near infrared light. In the case of the near infrared light used as the irradiation light L, an infrared camera is preferably used as the imaging device 20. The use of the infrared camera can capture the image for analysis in which the blood vessels are imaged in black, and the other regions such as skin are imaged in white.

The target part 2 is not necessarily irradiated with the irradiation light L when the image for analysis can be captured in which the boundaries between the blood vessels and the other regions are distinct without the irradiation with the irradiation light L.

The image for analysis of the target part 2 captured by the imaging device 20 is sent to the image processing device 31. The image processing device 31 subjects the image for analysis to image processing so as to acquire blood vessel information including the positions and the shapes of the blood vessels included in the target part 2.

Figure 2:
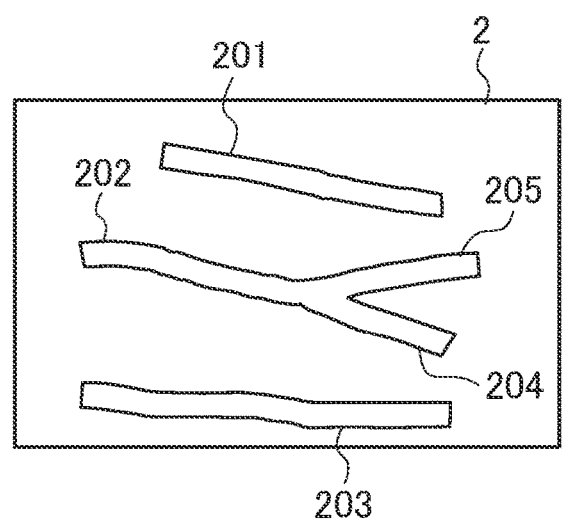
FIG. 2 is a schematic view showing an example of blood vessels included in a target part.

FIG. 2 illustrates the blood vessels included in the target part 2. FIG. 2 shows an example in which the blood vessel information on the blood vessels 201 to 205 is acquired. When a blood vessel is branched, the image processing device 31 acquires the blood vessel information such that a region from the branched part to an edge confirmable from the image for analysis is defined as one blood vessel. Namely, the blood vessel information is acquired for each blood vessel in which the region from the branched part to each edge is defined as the corresponding single blood vessel.

The image processing device 31 binarizes the image for analysis to distinguish the blood vessels from the other regions such as skin in accordance with a difference in luminance between the blood vessels and the other regions, for example, so as to acquire the blood vessel information. The image processing device 31 may binarize the image for analysis after executing image processing of emphasizing the contrast between the blood vessels and the other regions.

The evaluation device 32 uses the blood vessel information acquired by the image processing device 31 so as to assign a point rating regarding a parameter that indicates a conformity to a particular purpose with respect to the respective blood vessels included in the image for analysis depending on the degree of the conformity. For example, the rating points of the parameter to be assigned are greater as the degree of the conformity is higher. The specification device 33 specifies blood vessels conforming to the particular purpose from the blood vessels included in the target part 2 in accordance with the rating points of the parameter.

The parameter for assigning the point rating is determined depending on the intention of specifying the blood vessels. For example, when the intention is to specify the blood vessels easy to puncture by a needle, a parameter indicating the easiness of the needle puncture is used. Examples of parameters to be chosen include straightness of the blood vessels, an extending direction of the blood vessels, a length of the blood vessels, and a thickness of the blood vessels. The reason for using these parameters is as follows.

The needle puncture to a blood vessel is more difficult as the straightness of the blood vessel is lower. The blood vessel having higher straightness is thus preferably chosen for the needle puncture. The needle puncture is sometimes easier in a specific direction than in any other direction depending on the site of the blood vessel. For example, the needle puncture is easily performed on a forearm typically in the direction from the wrist to the elbow. The extending direction of the blood vessel thus often needs to be a particular direction (referred to below as a "conforming direction"). The needle puncture is more difficult as the blood vessel is shorter, while the needle puncture is easier as the blood vessel is thicker.

When the needle puncture needs to be performed on a part separated from a particular point in the target part 2, a distance from the particular point in the image for analysis may be used as a parameter for assigning the point rating. This can specify a blood vessel separated from a position difficult to puncture by a needle or a position at which the needle puncture needs to be avoided.

The evaluation device 32 assigns the higher points of the parameter to the blood vessels estimated to have the higher conformity to a particular purpose. For example, with regard to the parameter indicating the easiness of the needle puncture, the higher points of the parameter regarding the straightness of the blood vessels are assigned to the blood vessels having the higher straightness. Alternatively, the higher points of the parameter regarding the extending direction of the blood vessels may be assigned to the blood vessels as the extending direction is closer to the conforming direction. Similarly, the higher points of the parameter regarding the length of the blood vessels are assigned to the longer blood vessels, and the higher points of the parameter regarding the thickness of the blood vessels are assigned to the thicker blood vessels. In addition, the higher points of the parameter regarding the distance from the particular point in the image for analysis are assigned to the blood vessels having a longer distance from the particular point.

Various methods may be used for assigning the point rating regarding the parameter. For example, the highest points may be assigned to the blood vessel conforming to the particular purpose most, and the lower points may be assigned to the other vessels. With regard to the point rating of the parameter regarding the thickness of the blood vessels, for example, N points are assigned to the thickest blood vessel, and N−1 points are assigned to the next thickest blood vessel (N: an integer of two or greater).

Another method of assigning the point rating may be used that assigns N points to the thickest blood vessel, and assigns Nr points to the other blood vessels by use of a ratio r (0<r≤1) of the thickness of the other blood vessels to the thickness of the thickest blood vessel. For example, when the ratios of the thicknesses of the respective blood vessels are 1:0.98:0.97:0.95, 1 point, 0.98 points, 0.97 points, and 0.95 points of the parameter regarding the thickness of the blood vessels are assigned to the corresponding blood vessels. This can assign the point rating as a relative difference between the blood vessels, not assigning the point rating simply in accordance with the ranking regarding the thickness of the blood vessel.

Figure 3:
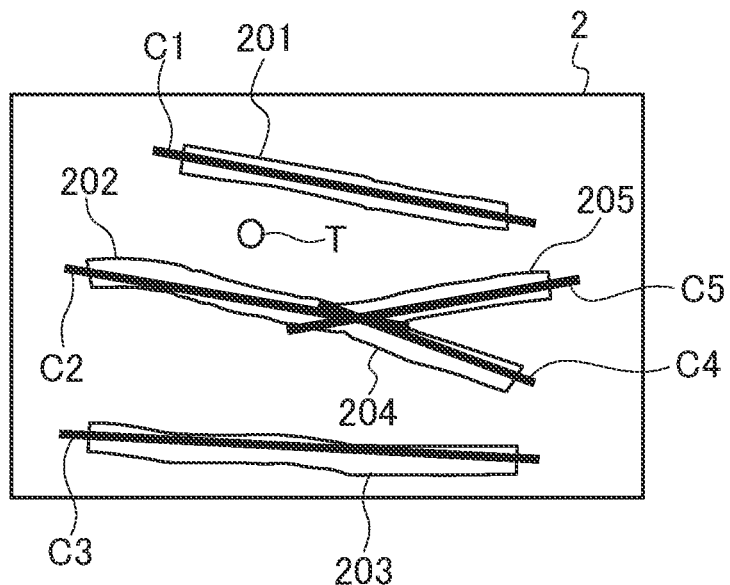
FIG. 3 is a schematic view showing an example of approximate lines of blood vessels created by the blood vessel specifying device according to the first embodiment of the present invention.

With regard to the evaluation of the straightness of the blood vessels, the evaluation device 32 creates approximate lines C1 to C5 corresponding to the blood vessels 201 to 205, as illustrated in FIG. 3. For example, the evaluation device 32 performs thinning on the blood vessels 201 to 205 in the binary image for analysis to obtain the approximate lines C1 to C5 of one pixel width by use of the method of least squares and the like. The evaluation device 32 then evaluates to determine that the straightness is higher as a coefficient of determination ($R^2$) obtained for the respective approximate lines C1 to C5 is closer to one, so as to assign the higher points of the parameter regarding the straightness to the corresponding blood vessels.

The extending direction of the respective blood vessels can be specified by use of the approximate lines described above. The evaluation device 32 assigns the higher points of the parameter regarding the extending direction to the blood vessels that each have a smaller angle between the extending direction of the approximate line and the conforming direction. The image for analysis may be obtained such that the conforming direction and the horizontal direction of the image for analysis are parallel to each other so as to specify the extending direction of the respective blood vessels.

The length of respective blood vessels is defined as a distance between one end to the other end of each blood vessel displayed in the image for analysis. For example, the approximate line of one pixel width may be created for each blood vessel, so as to define the number of pixels of the approximate line as the length of the blood vessel. The width of the respective blood vessels may be calculated by use of the approximate lines created for the respective blood vessels, for example. In particular, a perpendicular is drawn to the circumference from the approximate line, and the length of the part in which the perpendicular and the blood vessel overlap with each other is defined as the thickness of the blood vessel. When the thickness of the blood vessel varies, the thickest part may be defined as the thickness of the blood vessel, for example.

When the distance from the particular point in the image for analysis is used as the parameter, the particular point T is defined in the image for analysis, as illustrated in FIG. 3. The higher points of the parameter regarding the distance from the particular point T are assigned to the blood vessel as the shortest distance to the particular point T is longer.

The example is described in more detail below in which the evaluation device 32 assigns the point rating regarding the parameter indicating the easiness of the needle puncture so as to specify the blood vessels easy to puncture by a needle from the blood vessels 201 to 205 illustrated in FIG. 2. The present embodiment is illustrated below with a case in which the straightness of the blood vessels is defined as a first parameter P1, the extending direction of the blood vessels is defined as a second parameter P2, the length of the blood vessels is defined as a third parameter P3, the thickness of the blood vessels is defined as a fourth parameter P4, and the distance from the particular point in the image for analysis is defined as a fifth parameter P5.

The specification device 33 uses the parameter quantified in terms of points by the evaluation device 32 so as to assign the point rating to the respective blood vessels according to the following equation (1), for example:

$$S = P1 + P2 + P3 + P4 + P5 \quad (1)$$

The total points S of the blood vessel is 15 according to the equation (1) when the first parameter P1 of the corresponding blood vessel is three points, the second parameter P2 is five points, the third parameter P3 is four points, the fourth parameter P4 is one point, and the fifth parameter P5 is two points.

The parameter may be weighted depending on the purpose of specifying the blood vessels. In particular, the specification device 33 may calculate the total points S in which great importance is placed on the number of points regarding the parameter having a greater influence upon specifying the blood vessels conforming to a particular purpose. For example, the total points S are calculated according to the following equation (2):

$$S = a1 \times P1 + a2 \times P2 + a3 \times P3 + a4 \times P4 + a5 \times P5 \quad (2)$$

where the first weighting value a1 to the fifth weighting value a5 are determined depending on the degree of importance of the first parameter P1 to the fifth parameter P5.

For example, when the second parameter P2 regarding the extending direction of the blood vessels is regarded as important, while the fifth parameter P5 regarding the distance from the particular point does not need to be emphasized, the second weighting value a2 is set to be the largest among the other values in the equation (2), while the fifth weighting value a5 is set to be smaller than the other values. The total points S in this case are calculated according to the following equation (3), for example:

$$S = P1 + 2 \times P2 + P3 + P4 + 0.5 \times P5 \quad (3)$$

Weighting the parameters can change the conditions for the conforming blood vessels depending on the purpose of specifying the blood vessels.

Instead of the case in which the point rating is assigned with regard to all of the first parameter P1 to the fifth parameter P5 as described above, one of the first parameter P1 to the fifth parameter P5 may be chosen to assign the point rating. When the point rating is assigned with regard to the parameter indicating the easiness of the needle puncture to the blood vessels, at least one of the straightness of the blood vessels, the extending direction of the blood vessels, the length of the blood vessels, the thickness of the blood vessels, and the distance from the particular point is preferably chosen as the parameter for assigning the point rating.

As described above, the specification device 33 calculates the total points S of the respective blood vessels included in the target part 2 by use of the parameter quantified in terms of points by the evaluation device 32. The specification device 33 may rank the blood vessels included in the target part in the order of the conformity to the purpose through the comparison between the total points S. The information including the positions and the shapes of the approximate lines of the blood vessels, the rating points of the parameter, the total points S, and the ranking regarding the conformity is managed as a part of the blood vessel information on the respective blood vessels.

The specification device 33 uses the total points S calculated in accordance with the rating points of the parameter by the evaluation device 32, so as to specify the blood vessels conforming to a particular purpose among the blood vessels included in the target part 2 (referred to below as "conforming blood vessels"). For example, the blood vessel having the highest total points S is specified as the conforming blood vessel. Alternatively, all of the blood vessels having the higher total points S than predetermined points may be specified as the conforming blood vessels. Alternatively, the blood vessels ranked through the comparison of the total points S and determined to be in the top ranks within a predetermined range may be specified as the conforming blood vessels. The specification device 33 sends the information on the conforming blood vessels to the display device 40.

Figure 4:
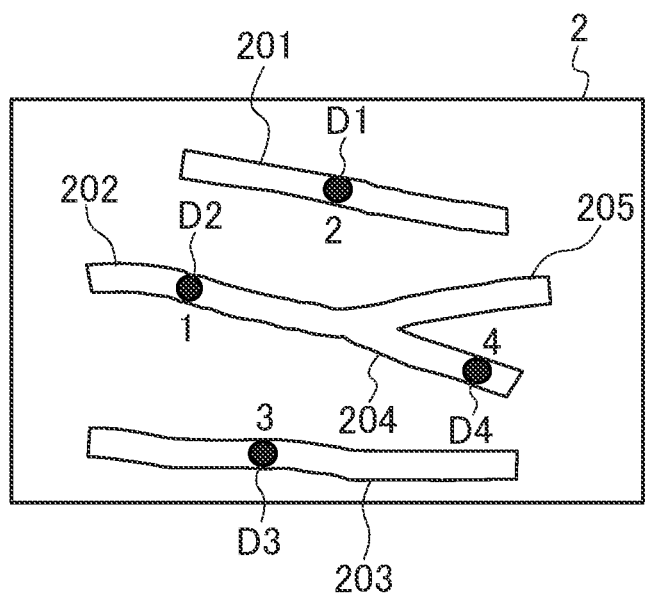
FIG. 4 is a schematic view showing an example of information on the blood vessels displayed by the blood vessel specifying device according to the first embodiment of the present invention.

The display device 40 displays the information of the conforming blood vessels sent from the specification device 33. For example, as illustrated in FIG. 4, the ranking of the blood vessels determined through the comparison of the total points S is displayed in figures on the display device 40 together with the images of the blood vessels included in the target part 2. Displaying the total points of the respective blood vessels is also effective instead of the ranking or in addition to the ranking. FIG. 4 illustrates the case of displaying the ranking of the blood vessels from the first place to the fourth place. In particular, the blood vessel 202 is the first place, the blood vessel 201 is the second place, the blood vessel 203 is the third place, and the blood vessel 204 is the fourth place. The blood vessel 205 is not specified as a conforming blood vessel, and the ranking is thus not displayed. For example, the blood vessel in which the rating points of the parameter do not fulfill a specific standard may be excluded from the conforming blood vessels.

The display device 40 may indicate a conforming site of each conforming blood vessel particularly suitable for a particular purpose along the entire blood vessel. In particular, a position easy to puncture by a needle in the respective conforming blood vessels may be indicated as the conforming site when the purpose is to specify the blood vessels easy to puncture by a needle. FIG. 4 illustrates the conforming sites D1 to D4 of the respective blood vessels 201 to 204 indicated by the black dots. For example, the thickest part in the blood vessel is indicated as the conforming site of the conforming blood vessel. Indicating the conforming site can specify the position easy to puncture by a needle in the blood vessel, so as to facilitate the needle puncture accordingly.

FIG. 4 illustrates the case in which the blood vessel 202 conforms to the purpose most. Ranking the blood vessels as described above can narrow the blood vessels so as to specify the blood vessels conforming to the particular purpose. In addition, displaying the ranking of the blood vessels by the display device 40 enables the confirmation of the positions of the other blood vessels as candidates instead of the blood vessel conforming to the purpose most.

As described above, the display device 40 displays the conforming sites and the ranking of the conforming blood vessels caused to overlap with the shapes of the conforming blood vessels, so as to visually recognize the information on the respective conforming blood vessels.

Figure 5:
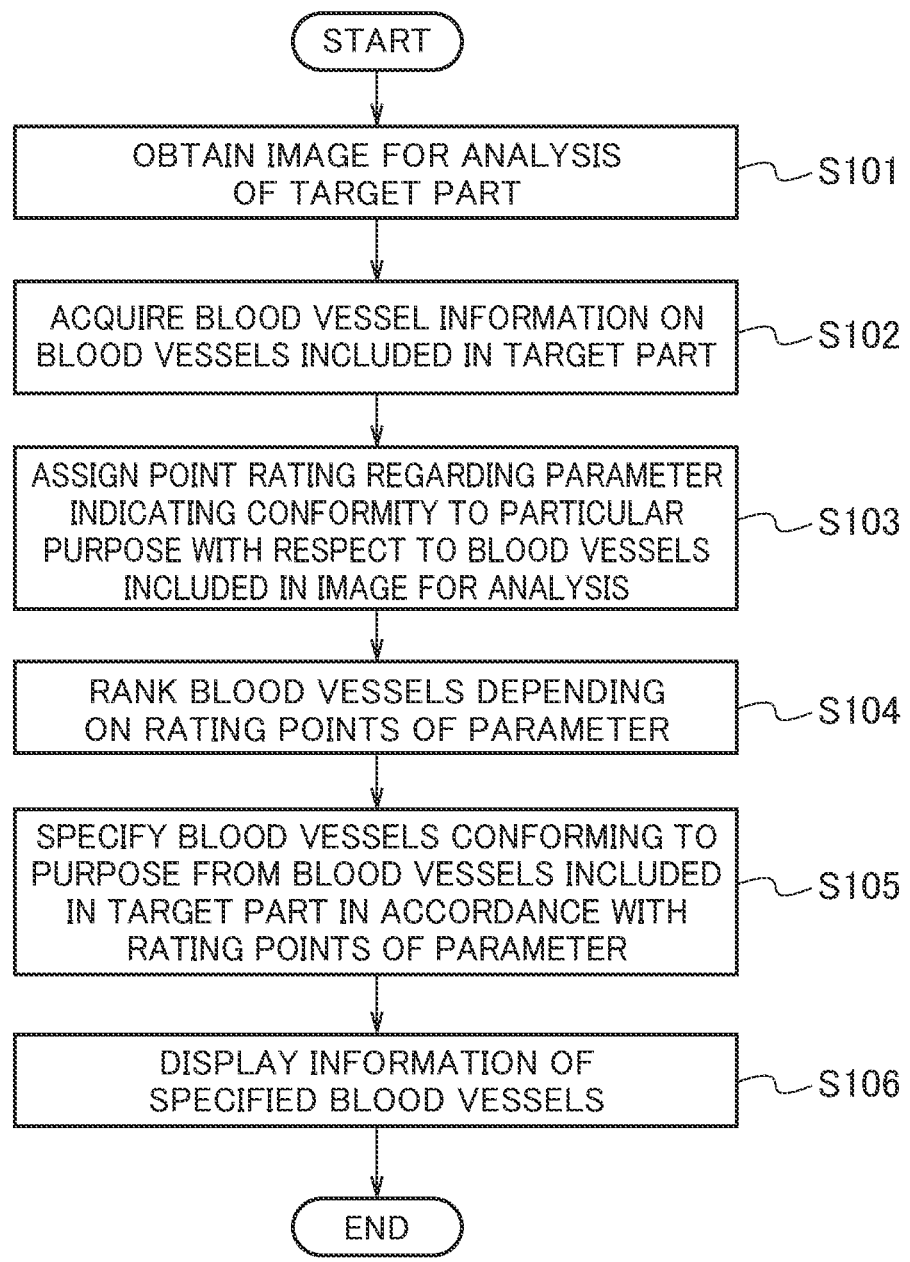
FIG. 5 is a flowchart for explaining a blood vessel specifying method according to the first embodiment of the present invention.

FIG. 5 is a flowchart explaining a series of processing by a blood vessel specifying method by use of the blood vessel specifying device 1.

In step S101 in the flowchart shown in FIG. 5, the imaging device 20 obtains the image for analysis of the target part 2.

The lighting device 10 at this point may irradiate the target part 2 with the irradiation light L having a specific wavelength.

In step S102, the image processing device 31 subjects the image for analysis to the image processing so as to acquire the blood vessel information including the positions and the shapes of the blood vessels included in the target part 2. In step S103, the evaluation device 32 uses the blood vessel information to assign the point rating regarding the parameter that indicates the conformity to a particular purpose with respect to the respective blood vessels included in the image for analysis. In step S104, the point rating regarding the parameter may be assigned to the respective blood vessels included in the target part 2 so that the blood vessels are ranked in the order of the conformity to the purpose in accordance with the assigned rating points of the parameter. In step S105, the specification device 33 then specifies the conforming blood vessels conforming to the purpose from the blood vessels included in the target part 2 in accordance with the rating points of the parameter.

In step S106, the display device 40 displays the information of the conforming blood vessels. The display device 40 may indicate the conforming sites of the respective conforming blood vessels together with the ranking of the blood vessels.

As described above, the blood vessel specifying device 1 according to the first embodiment assigns the point rating regarding the parameter that indicates the conformity to a particular purpose while referring to the image for analysis, and specifies the conforming blood vessels in accordance with the rating points of the parameter. The blood vessel specifying device 1 not only can visualize the blood vessels but also can specify the blood vessels conforming to a particular purpose. In addition, displaying the blood vessels with the ranked number can make a more precise determination on the blood vessels conforming to the purpose. Even if the blood vessel having the highest rating points of the parameter cannot be used, for example, the blood vessel specifying device 1 can easily choose the other blood vessels.

The point rating regarding the respective parameters described above does not lead the rating points of the parameters to be zero. The method of assigning the point rating based on the total points, however, could rank the blood vessel high that has a parameter not acceptable for a particular purpose such as blood collecting. To avoid such a risk, the rating points of the respective parameters may be led to be zero when exceeding a predetermined allowable range. In addition, the blood vessel in which any parameter is rated zero may be excluded from the conforming blood vessels. This can reduce or eliminate the risk of choosing the blood vessels as the conforming blood vessels that are not acceptable regarding a particular parameter.

Second Embodiment

Figure 6:
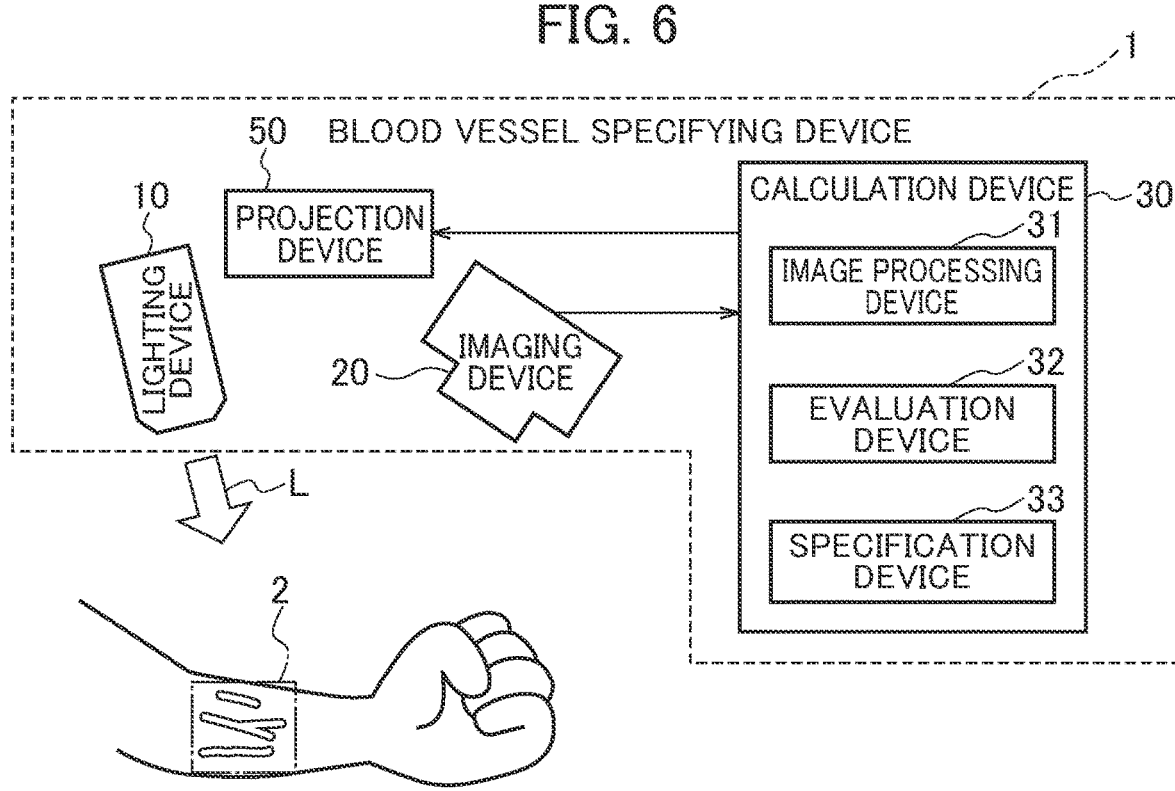
FIG. 6 is a schematic view illustrating a configuration of a blood vessel specifying device according to a second embodiment of the present invention.

The first embodiment is illustrated above with the case in which the information of the conforming blood vessels is displayed on the display device 40. The information of the conforming blood vessels may be projected on the target part 2 instead of or in addition to the information of the conforming blood vessels displayed on the display device 40. FIG. 6 illustrates a configuration of the blood vessel specifying device 1 according to a second embodiment that projects the information of the conforming blood vessels on the target part 2.

The blood vessel specifying device 1 illustrated in FIG. 6 differs from that illustrated in FIG. 1 in including, instead of the display device 40, a projection device 50 that projects the information of the conforming blood vessels on the target part 2. The other elements of the blood vessel specifying device 1 illustrated in FIG. 6 are the same as those in the first embodiment illustrated in FIG. 1. The blood vessel specifying device 1 according to the second embodiment may include the projection device 50 together with the display device 40.

Figure 7:
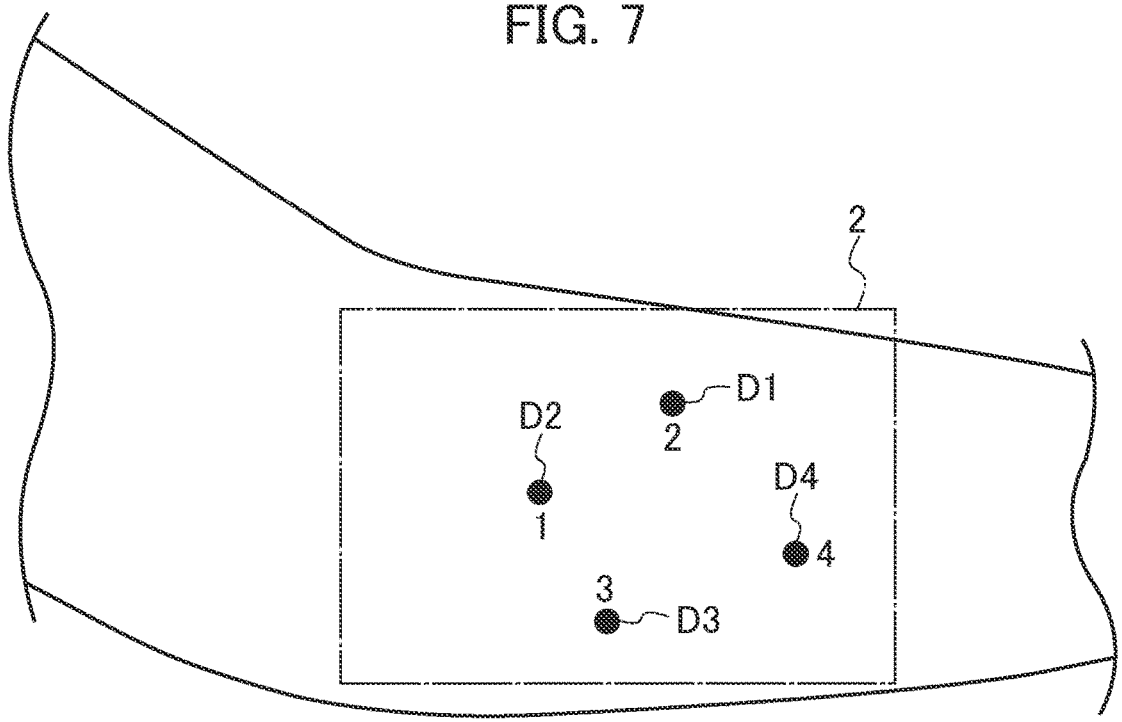
FIG. 7 is a schematic view showing an example of information of blood vessels projected on a target part by the blood vessel specifying device according to the second embodiment of the present invention.

As illustrated in FIG. 7, for example, the projection device 50 causes the positions of the conforming sites of the respective conforming blood vessels to correspond to the positions of the conforming blood vessels in the image for analysis so as to project the conforming sites and the ranking of the conforming blood vessels on the target part 2. FIG. 7 illustrates a case in which the blood vessels 201 to 204 are specified as the conforming blood vessels, and the conforming sites D1 to D4 of the blood vessels 201 to 204 are projected on the target part 2 together with the ranking of the blood vessels 201 to 204. This can clarify the positions easy to puncture by a needle, for example.

Figure 8:
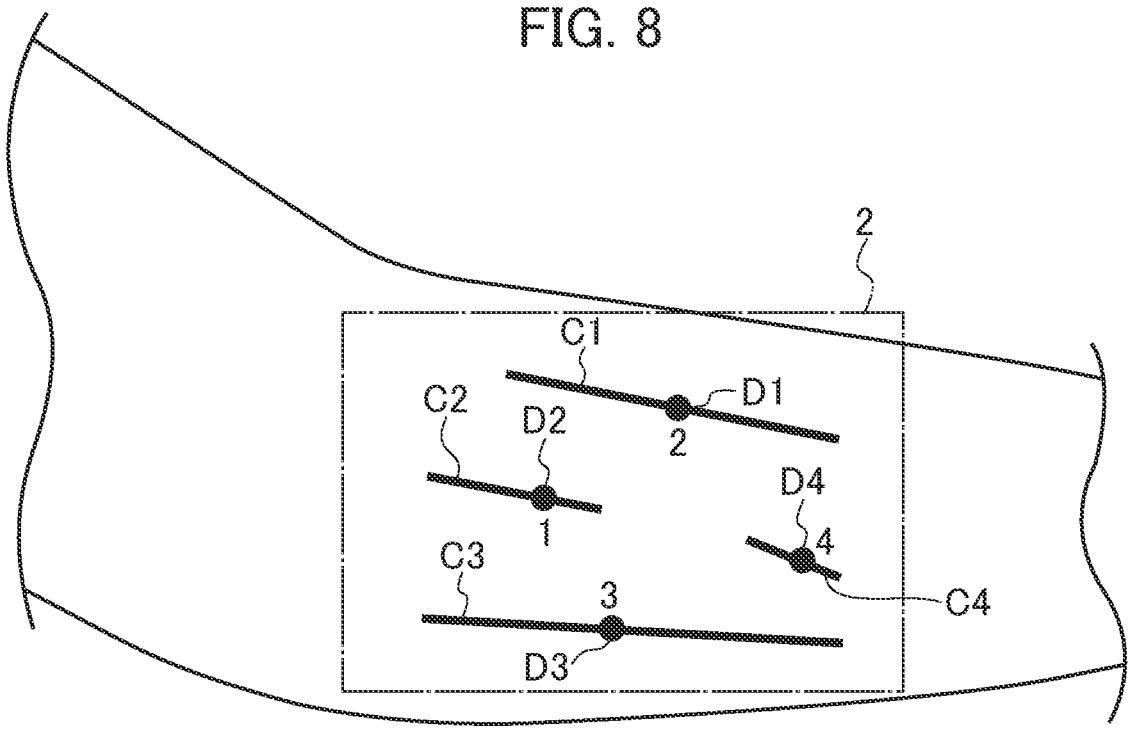
FIG. 8 is a schematic view showing another example of the information of the blood vessels projected on the target part by the blood vessel specifying device according to the second embodiment of the present invention.

Alternatively, as illustrated in FIG. 8, the projection device 50 may project the approximate lines of the shapes of the conforming blood vessels on the target part 2 together with the conforming sites or the ranking of the conforming blood vessels. The approximate lines are caused to correspond to the positions of the conforming blood vessels in the image for analysis so as to be projected on the target part 2. The approximate lines to be projected may correspond to the approximate lines created for evaluating the straightness of the blood vessels described above in the first embodiment, for example. FIG. 8 illustrates a case in which the blood vessels 201 to 204 are specified as the conforming blood vessels, and the approximate lines C1 to C4 of the shapes of the blood vessels 201 to 204 are displayed. Displaying the approximate lines facilitates the clear recognition of the positions of the conforming blood vessels. FIG. 8 illustrates the case in which the projection device 50 displays the conforming sites D1 to D4 overlapping with the approximate lines C1 to C4 of the conforming blood vessels.

Figure 9:
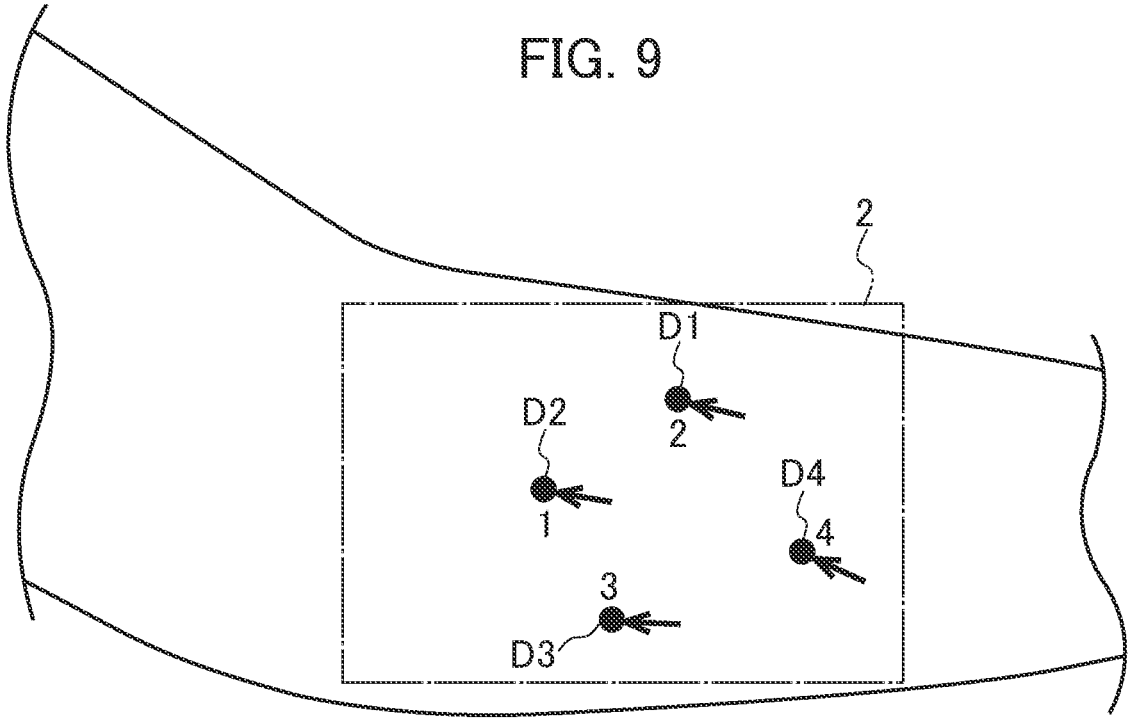
FIG. 9 is a schematic view showing still another example of the information of the blood vessels projected on the target part by the blood vessel specifying device according to the second embodiment of the present invention.

The directions of the respective blood vessels suitable for a particular purpose may be projected and indicated by arrows together with the conforming sites, as illustrated in FIG. 9. This indication facilitates the needle puncture to the blood vessels, for example. The directions of the respective blood vessels easy to puncture by a needle are each the extending direction of the blood vessels, for example.

FIG. 10 is a flowchart explaining a series of processing by a blood vessel specifying method by use of the blood vessel specifying device 1 according to the second embodiment.

The processing in step S101 to step S105 in the flowchart shown in FIG. 10 is the same as the processing in step S101 to step S105 in the flowchart shown in FIG. 5. After step S105 in the flowchart shown in FIG. 10, the projection device 50 projects the information of the conforming blood vessels on the target part 2 in step S107. In particular, the projection device 50 causes the specific sites, the ranking, and the approximate lines to correspond to the positions of the respective conforming blood vessels so as to project the information on the target part 2.

The blood vessel specifying device 1 according to the second embodiment can narrow the blood vessels conforming to a particular purpose while allowing the visual observation of the target part 2. The blood vessel specifying device 1 facilitates the recognition of the blood vessels easy to puncture by a needle and the conforming sites of the corresponding blood vessels, for example. The other configurations are substantially the same as those in the first embodiment, and overlapping explanations are not repeated below.

OTHER EMBODIMENTS

While the present invention has been described above with reference to the respective embodiments, it should be understood that the present invention is not intended to be limited to the descriptions and the drawings composing part of this disclosure. Various alternative embodiments, examples, and technical applications will be apparent to those skilled in the art according to this disclosure.

For example, the calculation device 30 of the blood vessel specifying device 1 may be installed at a place distant from a location for capturing the target part 2.

It should be understood that the present invention includes various embodiments not disclosed herein.

What is claimed is:

1. A blood vessel specifying method comprising:
   subjecting an image for analysis of a target part to image processing to acquire blood vessel information including positions and shapes of blood vessels included in the target part;
   using the blood vessel information to assign a point rating regarding a parameter that indicates a conformity to a particular purpose with respect to the blood vessels included in the image for analysis depending on a degree of the conformity, wherein the point rating is assigned regarding the parameter with respect to each of the blood vessels included in the target part, and the blood vessels are ranked in order of the conformity to the purpose;
   specifying conforming blood vessels conforming to the purpose from the blood vessels included in the target part in accordance with rating points of the parameter; and
   conforming sites of the conforming blood vessels conforming to the purpose are displayed together with at least either a ranking of the respective conforming blood vessels or total points of the parameter.

2. The blood vessel specifying method according to claim 1, wherein the point rating is assigned regarding the parameter that indicates easiness of a needle puncture to the blood vessels.

3. The blood vessel specifying method according to claim 2, wherein the point rating is assigned regarding, as the parameter, at least one of straightness of the blood vessels, a length of the blood vessels, a thickness of the blood vessels, an extending direction of the blood vessels, and a distance from a particular point in the image for analysis.

4. The blood vessel specifying method according to claim 1, wherein the rating points of the parameter that exceed a predetermined allowable range are led to be zero.

5. The blood vessel specifying method according to claim 1, wherein the conforming sites of the conforming blood vessels are displayed while the conforming sites are caused to overlap with shapes of the conforming blood vessels together with either the ranking or the total points.

6. The blood vessel specifying method according to claim 1, wherein the conforming sites of the conforming blood vessels are projected on the target part while the conforming sites are caused to correspond to the positions of the conforming blood vessels together with either the ranking or the total points.

7. The blood vessel specifying method according to claim 6, wherein the conforming sites caused to overlap with approximate lines of shapes of the conforming blood vessels are projected on the target part.

8. The blood vessel specifying method according to claim 1, wherein the parameter is weighted depending on the purpose.

9. The blood vessel specifying method according to claim 1, further comprising irradiating the target part with an irradiation light having a specific wavelength to capture the target part so as to obtain the image for analysis, wherein the specific wavelength is determined so that the image for analysis is obtained in which boundaries between the blood vessels and other regions are more distinct in the target part irradiated with the irradiation light than in another part not irradiated with the irradiation light.

10. The blood vessel specifying method according to claim 9, wherein the irradiation light is a near infrared light.

\* \* \* \* \*